United States Patent [19]

Maignan et al.

[11] Patent Number: 4,892,940
[45] Date of Patent: Jan. 9, 1990

[54] AROMATIC NAPHTHYL COMPOUNDS, A PROCESS FOR THEIR PREPARATION AND THEIR USE IN HUMAN AND VETERINARY MEDICINE AND IN COSMETIC COMPOSITIONS

[75] Inventors: Jean Maignan, Tremblay Les Gonesse; Gérard Lang, Saint Gratien; Gérard Malle, Villiers Sur Morin; Serge Restle, Aulnay-Sous-Boise; Braham Shroot, Antibes, all of France

[73] Assignee: L'Oreal, Paris, France

[21] Appl. No.: 52,930

[22] Filed: May 22, 1987

[30] Foreign Application Priority Data

May 23, 1986 [FR] France .................. 86 07405

[51] Int. Cl.$^4$ .............. C07C 69/80; C07C 43/20; A61K 7/48; A61K 31/19
[52] U.S. Cl. ............................ 536/55.2; 536/1.1; 560/8; 560/56; 560/100; 562/405; 562/490; 562/495; 564/172; 564/180; 568/659; 568/813; 514/23; 514/844; 514/859; 514/880; 424/70
[58] Field of Search ............ 536/55.2, 1.1; 560/8, 560/100, 56; 562/405, 490, 495; 564/172, 180; 568/659, 813; 514/23, 844, 859, 880; 424/70

[56] References Cited

U.S. PATENT DOCUMENTS

| | | | |
|---|---|---|---|
| 4,518,612 | 5/1985 | Bantick et al. | 514/533 |
| 4,717,720 | 1/1988 | Shroot et al. | 514/569 |
| 4,783,549 | 11/1988 | Lang et al. | 564/172 |

FOREIGN PATENT DOCUMENTS 324314   8/1975   Austria .

Primary Examiner—Ronald W. Griffin
Attorney, Agent, or Firm—Cushman, Darby & Cushman

[57] ABSTRACT

An aromatic naphthyl compound of the formula

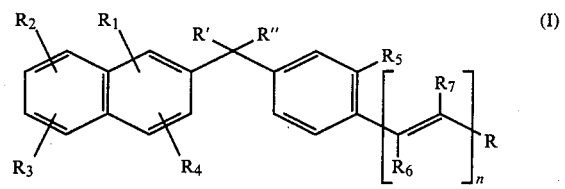

wherein
n is 0 or 1,
R' is hydrogen, OH, acyloxy, alkoxy or NH$_2$,
R" is hydrogen or lower alkoxy, or R' and R" taken together form an oxo, methano or hydroxy-imino radical,
R is —CH$_2$OH or —COR$_8$,
R$_8$ is hydrogen,

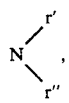

R$_9$ is hydrogen, alkyl having 1–20 carbon atoms, mono or polyhydroxyalkyl, aryl, aralkyl, the residue of a sugar or

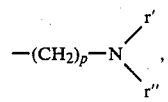

is 1, 2 or 3,
r' and r" each independently represent hydrogen, alkyl, monohydroxyalkyl, polyhydroxyalkyl, aryl, benzyl, the residue of amino acid or the residue of aminated sugar, or r' and r" together form a heterocycle,
R$_1$, R$_2$, R$_3$ and R$_4$ represent hydrogen, lower alkyl, alkoxy having 1–4 carbon atoms, fluoroalkoxy, CF$_3$, cycloalkyl, lower acyl, halogen, OH, amino, acylamino or alkoxy carbonyl,
R$_5$, R$_6$ and R$_7$ represent hydrogen or methyl or when n=1, R$_5$ and R$_7$ taken together can form with the benzene ring a naphthalene ring, and the salts of the compound of formula I or their geometric or optical isomers.

These compounds are useful in human and veterinary medicine and in cosmetic compositions.

28 Claims, No Drawings

AROMATIC NAPHTHYL COMPOUNDS, A PROCESS FOR THEIR PREPARATION AND THEIR USE IN HUMAN AND VETERINARY MEDICINE AND IN COSMETIC COMPOSITIONS

The present invention has for an object new aromatic naphthyl compounds, a process for their preparation and their use in human and veterinary medicine and in cosmetic compositions.

These new compounds find a use in the topical and systemic treatment of dermatologic diseases linked to a keratinization disorder (differentiation-proliferation) and dermatologic diseases, or others, having an inflammatory and/or immunoallergic component and in the treatment of illnesses of the degeneration of conjunctive tissue. They also exhibit anti-tumor activity.

Moreover, these compounds can be employed in the treatment of atophy, be it cutaneous or respiratory, and in the treatment of rheumatoid psoriasis.

These compounds also possess good activity against the germs involved in acne.

Finally, the compounds of the present invention are usefully employed in the opthamology field and principally in the treatment of corneopathies.

The aromatic naphthyl compounds of the present invention can be represented by the formula:

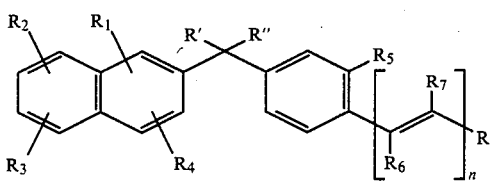
(I)

wherein:

n is 0 or 1,

R' represents hydrogen, OH, acyloxy, lower alkoxy or NH$_2$,

R" represents hydrogen, or lower alkoxy, or R' and R" taken together form an oxo radical (=O), a methano radical (=CH$_2$) or a hydroxyimino radical (=N-OH), R represents —CH$_2$OH or 'COR$_8$, R$_8$ represents hydrogen, —OR$_9$ or

R$_9$ represents hydrogen, linear or branched alkyl having 1-20 carbon atoms, mono or polyhydroxy alkyl, aryl or aralkyl optionally substituted, or the residue of a sugar or even the radical

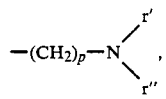

p is 1, 2 or 3, r' and r" each independently represent hydrogen, lower alkyl, monohydroxy alkyl optionally interrupted by a heteroatom, or polyhydroxy alkyl, aryl or benzyl optionally substituted, the residue of an amino acid or an aminated sugar, or together form a heterocycle, R$_1$, R$_2$, R$_3$ and R$_4$, each independently, represent hydrogen, lower alkyl, alkoxy having 1-4 carbon atoms, lower fluoroalkoxy, —CF$_3$, cycloalkyl, lower acyl, halogen, OH, amino optionally substituted, lower acylamino or lower alkoxy carbonyl, the said substituents R$_1$-R$_4$ being able to be distributed on one of the two rings or on both at the same time, R$_5$, R$_6$ and R$_7$ represent hydrogen or methyl or when n=1, R$_5$ and R$_7$, taken together, can form with the benzene ring a naphthalenic ring (R$_5$—R$_7$=—CH=-CH—), and the salts of said compounds of formula I, as well as their geometric and optical isomers.

By lower alkyl radical is meant an alkyl radical having 1-6 carbon atoms and principally methyl, ethyl, isopropyl, butyl and tert. butyl.

By monohydroxyalkyl is meant a radical having 2-6 carbon atoms and principally 2-hydroxy ethyl, 2-hydroxy propyl or 2-hydroxy ethoxyethyl.

By polyhydroxy alkyl is meant a radical containing 3-6 carbon atoms and 2-5 hydroxy groups such as 1,3-dihydroxy propyl, 2,3-dihydroxy propyl, or the residue of pentaerythritol.

By aryl is meant phenyl optionally substituted by halogen, hydroxy or nito.

By residue of an amino acid is meant a residue derived, for example, from α- or β-alanine or from methionine.

By residue of a sugar is meant a residue derived from, for example, glucose, mannose, erythrose or galactose.

By residue of an aminated sugar is meant a residue derived, for example, from glucosamine, galactosamine or mannosamine.

When the radicals r' and r" taken together form a heterocycle, the heterocycle is, preferably, piperidino, piperazino, mopholino, pyrrolidino or 4-(2-hydroxyethyl) piperazino.

By cycloalkyl is meant a radical having 5-12 carbon atoms and principally cyclopentyl, cyclohexyl or adamantyl.

The lower alkoxy radical is one having 1-4 carbon atoms and preferably methoxy, ethoxy, isopropoxy or tert.butoxy.

The lower acyl radical is preferably acetyl or propionyl.

The halogen is chlorine, bromine or fluorine.

When the compounds according to the present invention are provided in the form of salts, they can be salts of an alkali or alkaline earth metal or even of zinc, or of an organic amine when they carry at least one free acid function, or of salts of a mineral or organic acid, principally the hydrochloride, hydrobromide or citrate when they carry at least one amine function.

In accordance with a preferred embodiment of the present invention the compounds correspond to one of the following formulas:

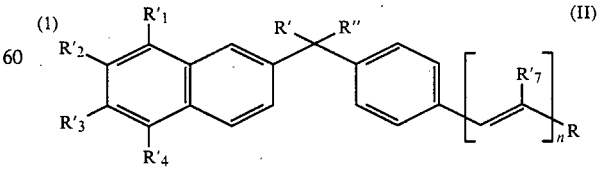
(II)

wherein n is 0 or 1,

R'$_1$, R'$_2$ and R'$_4$ represent hydrogen or lower alkyl,

R'hd 3 represents lower alkyl or lower alkoxy,
R' represents hydrogen or OH and
R" represents hydrogen, or
R' and R" together form an oxo radical (=O) and R represents —CH₂OH or COR'₈,
R'₈ represents —OR₉' or

R'₉ represents hydrogen or lower alkyl,
r' is hydrogen and
r" is lower alkyl; and (2) 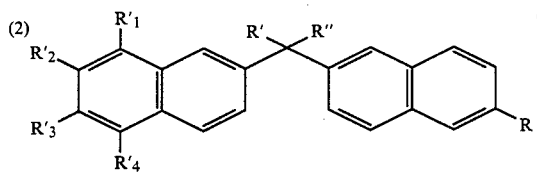 (III)

wherein
R, R', R", R'₁, R'₂, R'₃ and R'₄ have the meaning given above for the compound of formula II.

Representative compounds of formula I above include the following:

(1) 2-methyl 6-(6,7-dimethyl2-naphthyl) carbonyl naphthalene carboxylate,
(2) 6-(6,7-dimethyl-2-naphthyl) carbonyl-2-naphthalene carboxylic acid,
(3) 2-methyl 6-(5,8-dimethyl-6-methoxy-2-naphthyl) carbonyl naphthalene carboxylate,
(4) 6-(5,8-dimethyl-6-methoxy-2-naphthyl) carbonyl-2-naphthalene carboxylic acid,
(5) N-ethyl-6-(5,8-dimethyl-6-methoxy-2-naphthyl) carbonyl-2-naphthalene carboxamide,
(6) 6-(6-methoxy-2-naphthyl) carbonyl-2-methyl naphthalene carboxylate,
(7) 6-(6-methoxy-2-naphthyl) carbonyl-2-naphthalene carboxylic acid,
(8) 6-(5,8-dimethyl-6-methoxy-2-naphthyl) hydroxymethyl-2-naphthalene carboxylic acid,
(9) N-ethyl-6-(5,8-dimethyl-6-methoxy-2-naphthyl) hydroxymethyl-2-naphthalene carboxamide,
(10) 6-(5,8-dimethyl-6-methoxy-2-naphthyl) hydroxy methyl-2-naphthalene carbinol,
(11) trans ethyl-4-(5,8-dimethyl-6-methoxy-2-naphthyl) carbonyl-α-methyl cinnamate,
(12) trans-4-(5,8-dimethyl-6-methoxy-2-naphthyl) carbonyl-α-methylcinnamic acid,
(13) N-ethyl trans 4-(5,8-dimethyl-6-methoxy-2-naphthyl) carbonyl-α-methyl cinnamide,
(14) trans 4-(5,8-dimethyl-6-methoxy-2-naphthyl) hydroxy methyl-α-methyl cinnamic acid,
(15) methyl 4-(5,8-dimethyl-6-methoxy-2-naphthyl) carbonyl benzoate,
(16) 4-(5,8-dimethyl-6-methoxy-2-naphthyl) carbonyl benzoic acid,
(17) 4-(5,8-dimethyl-6-methoxy-2-naphthyl) hydroxymethyl benzoic acid,
(18) 4-(5,8-dimethyl-6-methoxy-2-naphthyl) hydroxymethyl phenyl carbinol,
(19) 4-(5,8-dimethyl-6-methoxy-2-naphthyl) carbonyl benzaldehyde,
(20) N-ethyl-4-(5,8-dimethyl-6-methoxy-2-naphthyl) carbonyl benzamide,
(21) 1-(5,8-dimethyl-6-methoxy-2-naphthyl)-1-(6-carboxy-2-naphthyl) methane and
(22) 1-(5,8-dimethyl-6-methoxy-2-naphthyl)-1-(6-N-ethyl carboxamide-2-naphthyl)methane.

The present invention also relates to a process for preparing the compounds of formula I defined above.

The compounds of formula I wherein R' and R" together form an oxo radical and n=0 are obtained in accordance with the following reaction scheme:

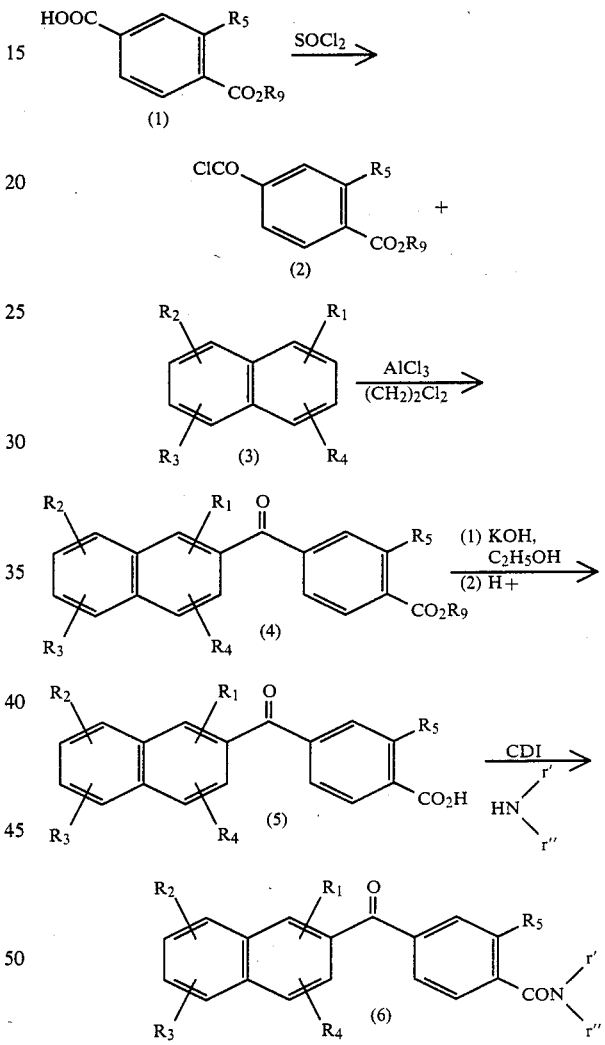

R=alkyl having 1–20 carbon atoms.

The starting 4-alkoxy carbonyl benzoic acid (1) is obtained by oxidation of alkyl 4-formyl benzoate, preferably methyl 4-formyl benzoate which is a commercial product.

The corresponding acid chloride is prepared by the action of thionyl chloride in accordance with conventional procedures for the preparation of acid chlorides.

The condensation reaction of 4-alkoxy carbonyl benzoic acid chloride (2) on the naphthalenic derivative (3) is carried out under Friedel-Crafts reaction conditions, i.e. in the presence of anhydrous aluminum chloride in an organic solvent such as 1,2-dichloroethane at a temperature between 0° and 25° C. with stirring.

Starting with the ester (4) there is obtained by saponification the corresponding acid (5) which can then be transformed into the amide of formula (6) by the action of an amine having the formula

in the presence of N,N'-carbonyldiimidazole (CDI).

For certain values of $R_9$ in formula I and in particular when $R_9$ represents a monohydroxy or polyhydroxy alkyl radical, it is preferable to prepare the acid (5) starting with the methyl ester (4), ($R_9=CH_3$) and then esterify the resulting acid to the ester of the selected alcohol in accordance with known procedures.

When, in the compounds of formula I, n=1, they are obtained in accordance with the following reaction scheme:

The compounds of formula I wherein R'=OH and R''=H are obtained starting with ketonic derivatives by reduction with sodium borohyride in THF.

The compounds of formula I wherein R'=R''=H are obtained by reduction with zinc of the ketonic derivatives, in acetic acid, in the presence of HCl.

These reduction reactions of the carbonyl must, however, be compatible with the nature of the various substituents ($R_1$ to $R_7$) as well as with the radical R. It can be desirable to ensure optional protection, however the reduction of the carbonyl creates no difficulty when R=—$CO_2H$.

The acyloxy derivatives of the compounds of formula I (R'=$C_1$-$C_4$ acyloxy and R''=H) are obtained by reacting an activated form of the acid such as an anhydride or acid chloride with a compound of formula I wherein R'=OH and R''=H.

The alkoxy derivatives of the compounds of formula I (R'=$C_1$-$C_4$ alkoxy and R''=H) are also obtained starting with the compounds of formula I (R'=OH and R''=H) in accordance with known methods.

For the preparation of the acyloxy and alkoxy derivatives it is preferable that the radical R is an ester, acid or amide function.

The compounds of formula III wherein R', and R'' together form an oxo radical are obtained in accordance with the following reaction scheme:

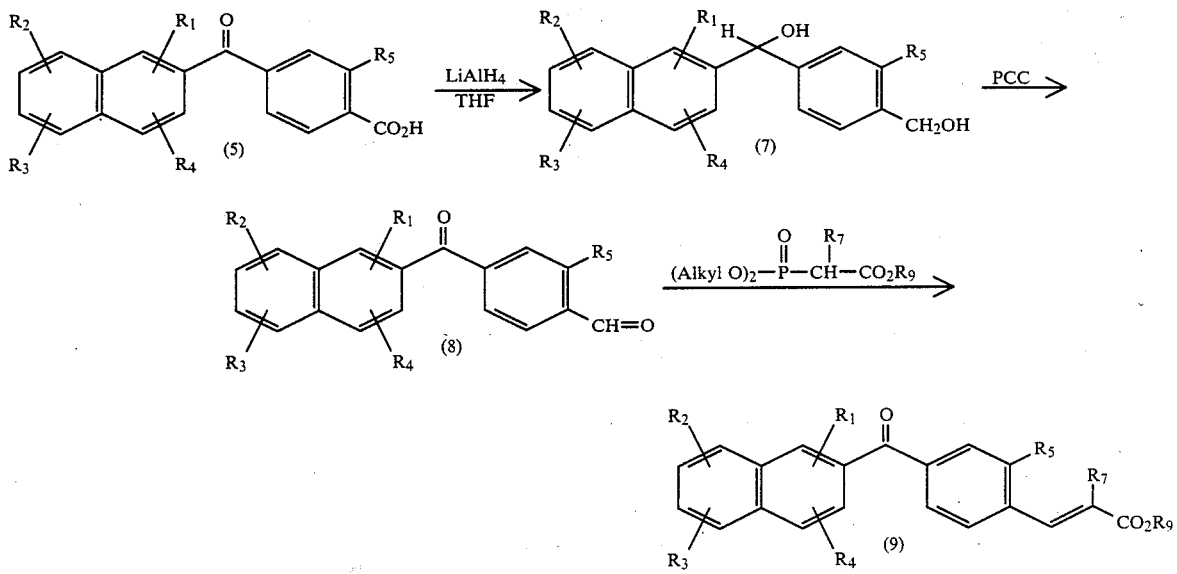

The keto-acid (5) is reduced, in the presence of lithium aluminum hydride, to the corresponding diol (7) which is then oxidized, in the presence of pyridinium chlorochromate (PCC), to the keto-aldehyde (8). The latter, by the Wittig-Horner reaction with an alkyl phosphono acetate, substituted or not, provides in the presence of sodium hydride in an organic solvent such as THF, the unsaturated ester of formula (9).

The ester of formula (9) can then be transformed, as before, into the corresponding acid and then into the amide by reaction with an amine of the formula

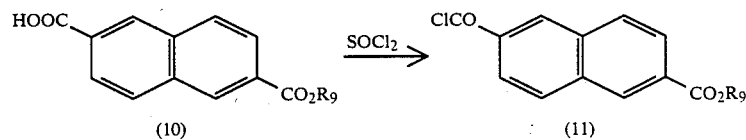

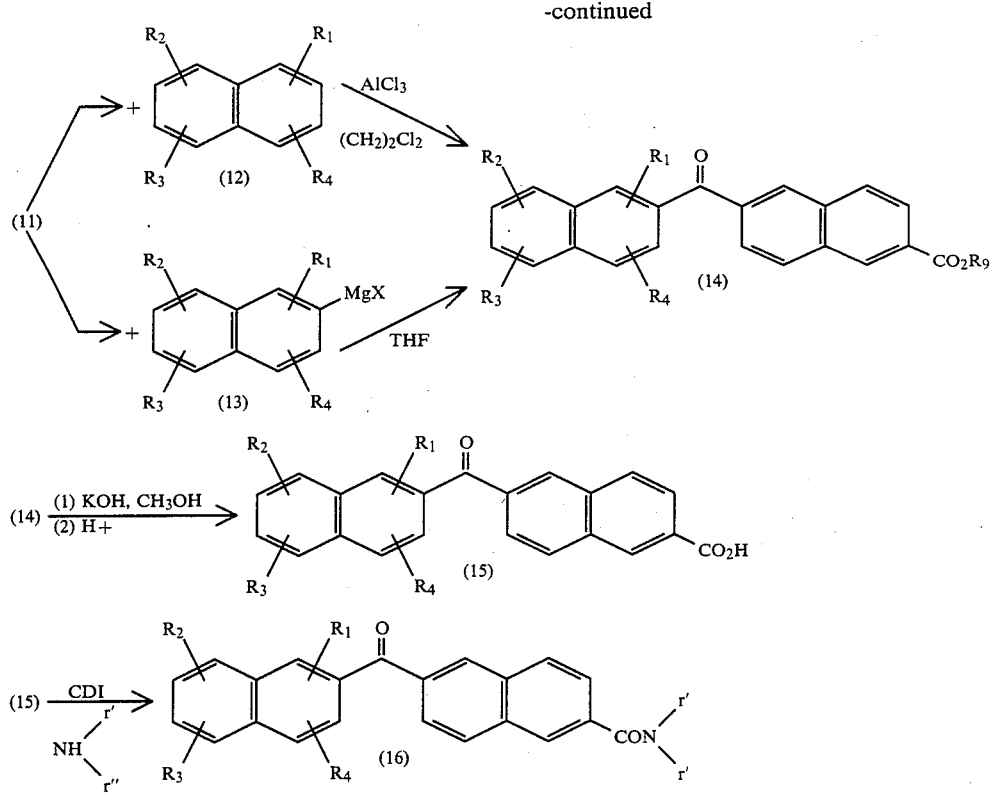

$X = Br$ or $Cl$ and $R_9 = C_1-C_{20}$ alkyl.

The starting 6-alkoxy carbonyl-2-naphthalene carboxylic acid (10) is obtained by the monosaponification reaction of 2,6-alkyl naphthalene carboxylate, preferably starting with 2,6-methyl naphthalene dicarboxylate which is a commercial product. The corresponding acid chloride (11) is prepared by the action of thionyl chloride in accordance with known methods for the preparation of acid chlorides.

The condensation reaction of the 6-alkoxy carbonyl-2naphthalene carboxylic acid chloride (11) can be effected either on the naphthalenic derivative (12) under Friedel-Crafts reaction conditions, or on the magnesium derivative of the naphthalenic halogeno derivative (13).

The Friedel-Crafts reaction conditions are the same as those given above for the preparation of the compounds of formula (4). The preparation of the magnesium derivative of the naphthalenic halogeno derivative (13) is carried out in anhydrous THF at reflux and the condensation of the acid chloride is carried out at a temperature of about 0° C in the same solvent.

In accordance with the same methods as those described above for the compounds of formula I there can be prepared other compounds of formula III, i.e. those of formulas (15) and (16) as well as compounds of formula III wherein R' and R", taken together, are other than the oxo radical.

The present invention also relates to a medicine comprising the compounds of formula I defined above.

These compounds exhibit excellent activity in the inhibition test of ornithine decarboxylase in nude rats, after induction, by "tape stripping", M. Bouclier et al, Dermatologica, 169, No. 4, 1984. This test is recognized as a measure of an antiproliferative activity.

These compounds are particularly appropriate for treating dermatologic ailments linked to a keratinization disorder (differentiation-proliferation) as well as dermatologic diseases, or others, having an inflammatory and/or immunoallergic component, and principally:

*acne vulgaris,* comedons or polymorphs, solar senile acne and medicinal or professional acne, extensive and/or severe forms of psoriasis and other keratinization disorders, and principally ichtysoses and ichtysosis-like conditions, Darier malady, palmo-plantar keratodermies, leucophasies and leucophasie-like states, lichen plan, all malignant or benign dermatologic proliferations, severe or extensive.

They are also active in the treatment of tumors, of rheumatoid psoriasis, cutaneous or respiratory atophies as well as in certain opthalmologic problems relating to corneopathies.

Thus, the present invention also relates to medicinal compositions containing at least one compound of formula I, such as defined above, or one of its salts or one of its isomers.

The present invention thus relates to a new medicinal composition, intended principally for the treatment of the abovementioned disorders, comprising in a pharmaceutically acceptable support, an effective amount of at least one compound of formula I and/or one of its salts and/or one of its isomers.

The compounds of the present invention of formula I wherein $n=0$ as well as compounds of formula III exhibit good stability to light and oxygen.

The compounds according to the present invention are generally administered at a daily dosage of about 2 $\mu g/kg$ to 2 $mg/kg$ of body weight.

As the support or carrier for these compositions any conventional carrier can be employed, the active component being found either in the dissolved state, or in the dispersed state in said carrier.

The administration of the compounds of the present invention can be effected enterally, parenterally, topically or ocularly.

When administered enterally, the medicines can be provided in the form of tablets, gelules, lozenges, syrups, suspensions, solutions, powders, granules or emulsions.

When administered parenterally, the medicinal compositions can be provided in the form of solutions or suspensions for perfusion or injection.

When administered topically, the pharmaceutical compositions, based on the compounds according to the present invention, can be provided in the form of ointments, tinctures, creams, salves, powders, pads, impregnated tampons, solutions, lotion, gels, sprays or suspensions.

These compositions for topical administration can be provided under anhydrous form or in aqueous form according to clinical indications.

When administered ocularly, the composition is provided principally in the form of an eyewash.

The compositions for topical or ocular administration contain preferably from 0.005 to 5 percent by weight of at least one compound of formula I, defined above, based on the total weight of the composition.

The compounds of formula I, according to the present invention, are also useful in the cosmetic field, and in particular in body and hair hygiene compositions and principally for the treatment of skin having acne tendencies, to improve the growth of hair, to combat hair loss, to combat against an oily appearance of the skin or hair, in the prevention or treatment of the harmful effects of the sun or in the treatment of physiologically dry skin.

The present invention thus relates to a cosmetic composition containing, in a cosmetically acceptable vehicle, an effective amount of at least one compound of formula I or one of its salts and/or one of its isomers, this composition being provided principally in the form of a lotion, cream, gel, soap or shampoo.

The concentration of the compound of formula I in these cosmetic compositions is between 0.0005 and 2 weight percent and preferably between 0.01 and 1 weight percent based on the total weight of the composition.

The medicinal and cosmetic compositions according to the present invention can contain inert or even pharmacodynamic or cosmetically active additives and, principally: hydrating agents such as thiamorpholinone and its derivatives or urea; antiseborrheic or anti-acne agents such as S-carboxymethylcysteine, S-benzylcysteamine, their salts and their derivatives, tioxolone or benzoyl peroxide; antibiotics such as erthromycin and its esters, neomycin, tetracyclines and 4,5-polymethylene- 3-isothiazolones; agents promoting the growth of hair such as "Minoxidil" (2,4-diamino-6-piperidino-3-pyrimidine oxide) and its derivatives, Diazoxide (7-chloro-3-methyl-1,2,4-benzothiadiazine-1,1-dioxide) and Phenytoin (5,5-diphenyl-2,4-imidazolidine dione); steroidal and non-steroidal anti-inflammatory agents; carotenoids and, principally, $\beta$-carotene; anti-psoriasic agents such as anthralin and its derivatives, 5,8,11,14-eicosatetraynoic and 5,8,11-eicosatriynoic acids, their esters and their amides.

The compositions according to the present invention can also include flavor improving agents, preservatives, stabilizers, humidity regulating agents, pH regulating agents, osmotic pressure modifying agents, emulsifiers, UV-A and UV-B filters, antioxidants such as $\alpha$-tocopherol, butylhydroxy anisole or butylhydroxy toluene.

The following nonlimiting examples illustrate the preparation of the active compounds of formula I according to the present invention as well as compositions containing these compounds.

EXAMPLE 1

Preparation of 2-methyl 6-(5,8-dimethyl-6-methoxy-2-naphthyl) carbonyl naphthalene carboxylate.

Compound of formula III wherein R' and R''=oxo, $R'_1=R'_4=CH_3$, $R'_2=H$, $R'=OCH_3$ and $R=-CO_2CH_3$ To a suspension of 1.86 g ( 10 mmoles) of 1,4-dimethyl-2methoxy naphthalene and 2.49 g (10 mmoles) of 6-methoxycarbonyl-2-naphthalene carboxylic acid chloride in 60 cm$^3$ of anhydrous 1,2-dichloroethane, there are added in portions 1.87 g (14 mmoles) of anhydrous aluminum chloride. The mixture is stirred for 5 hours at ambient temperature and then poured into 100 cm$^3$ of acidulated ice water. The organic phase is decanted. The aqueous phase is extracted twice with 80 cm$^3$ of dichloroethane. The dichloroethane phases are combined, washed with sodium bicarbonate, dried on sodium sulfate, and then concentrated under reduced pressure. The resulting solid is purified by chromatography on silica gel 60, eluted with a 70/30 mixture of dichloromethane/toluene, and then recrystallized in acetonitrile. After drying, 1.3 g of yellow crystals of 2-methyl 6-(5,8-dimethyl-6-methoxy-2-naphthyl) carbonyl naphthalene carboxylate having a melting point of 179° C. are obtained.

The NMR$^1$H 60 MHz spectrum conforms to the expected structure.

Elemental analysis: $C_{26}H_{25}O_4$

|  | C | H | O |
|---|---|---|---|
| Calculated: | 78.37 | 5.57 | 16.06 |
| Found: | 77.75 | 6.26 | 15.68 |

EXAMPLE 2

Preparation of 2-methyl 6-(6,7-dimethyl-2-naphthyl) carbonyl naphthalene carboxylate. Compound of formula III wherein R' and R''=oxo, $R'_1=R'_4=H$, $R'_2=R'_3=CH_3$ and $R=-CO_2CH_3$ To a suspension of 2.3 g (12 mmoles) of 2,3-dimethyl naphthalene and 3 g (12 mmoles) of 6-methoxycarbonyl-2-naphthalene carboxylic acid chloride in 60 cm$^3$ of anhydrous 1,2-dichloroethane, there are added in portions 3.2 g (24 mmoles) of anhydrous aluminum chloride. The mixture is stirred for 5 hours at ambient temperature and then poured into 100 cm$^3$ of acidulated ice water. The organic phase is decanted. The aqueous phase is extracted twice with 60 cm$^3$ of dichloroethane. The dichloroethane phases are combined, washed with sodium bicarbonate, dried on sodium sulfate and then concentrated under reduced pressure. The resulting solid is then purified by chromatography on silica gel 60, eluted with a 60/40 dichloromethane/toluene mixture and then recrystallized in methanol. After drying, 1.3 g of yellow crystals of 2-methyl 6(6,7-dimethyl-2-naphthyl) carbonyl naphthalene carboxylate having a melting point of 176° C. are obtained.

The NMR$^1$H 60 MHz spectrum conforms to the expected structure.

Elemental analysis: $C_{25}H_{20}O_3$

|  | C | H | O |
|---|---|---|---|
| Calculated: | 81.50 | 5.47 | 13.03 |
| Found: | 81.48 | 5.44 | 13.28 |

EXAMPLE 3

Preparation of 2-methyl 6-(6-methoxy-2-naphthyl) carbonyl naphthalene carboxylate. Compound of formula III wherein R' and R''=oxo, $R'_1=R'_2=R'_4=H$, $R'_3=OCH_3$ and $R=CO_2CH_3$ To a suspension of 2.06 g (13 mmoles) of 2-methoxy naphthalene and 3.23 g (13 mmoles) of 6-methoxycarbonyl-2-naphthalene carboxylic acid chloride in 80 cm³ of anhydrous 1,2dichloroethane, there are added by portions 3.23 g (25 mmoles) of anhydrous aluminum chloride. The mixture is stirred for 5 hours at ambient temperature and then poured into 150 cm³ of acidulated ice water. The organic phase is decanted. The aqueous phase is extracted twice with 60 cm³ of dichloroethane. The dichloroethane phases are combined, washed with sodium bicarbonate, dried on sodium sulfate and then concentrated under reduced pressure. The resulting solid is purifed by two successive recrystallizations in methanol. After drying, 1.95 g of yellow crystals of 2-methyl 6-(6-methoxy-2-naphthyl) carbonyl naphthalene carboxylate having a melting point of 160° C are obtained.

The NMR$^1$H 60 MHz spectrum conforms to the expected structure.

Elemental analysis: $C_{24}H_{18}O_4$

|  | C | H | O |
|---|---|---|---|
| Calculated: | 77.82 | 4.90 | 17.28 |
| Found: | 77.95 | 4.91 | 17.15 |

Example 4

Preparation of 6-(5,8-dimethyl-6-methoxy-2-naphthyl) carbonyl-2-naphthalene carboxylic acid. Compound of fomrula III wherein R'and R''=oxo, $R'_1-R'_4=CH_3$, $R'_2=H$, $R'_3=OCH_3$ and $R=CO_2H$ A suspension of 1.15 g (2.86 mmoles) of 2-methyl 6-(5,8-dimethyl-6-methoxy-2-naphthyl) carbonyl naphthalene carboxylate, obtained in Example 1, is stirred for 3 hours in a mixture of 30 cm³ of alcohol and 30 cm³ of 6N aqueous potash heated at reflux. After having added 100 cm³ of water, the alcohol is removed by evaporation under a vacuum. The resulting aqueous phase is diluted to 500 cm³, cooled to a temperature between 0 and 5° C. and then acidified with 30 cm³ of 12 N HCl. The resulting precipitate is filtered, washed with water and dried at 80° C. on potash. After recrystallization in methyl ethyl ketone containing a little acetic acid, 0.77 g of beige crystals of 6-(5,8-dimethyl-6-methoxy-2-naphthyl) carbonyl-2- naphthalene carboxylic acid having a melting point of 273° C. is obtained.

The NMR$^1$H 250 MHz spectrum conforms to the expected structure.

Elemental analysis: $C_{25}H_{20}O_4$

|  | C | H | O |
|---|---|---|---|
| Calculated: | 78.16 | 5.25 | 16.64 |
| Found: | 77.52 | 5.88 | 16.43 |

EXAMPLE 5

Preparation of 6-(6,7-dimethyl-2-naphthyl) carbonyl-2-naphthalene carboxylic,acid. Compound of formula III wherein R' and R''=oxo, $R'_1=R'_4=H$, $R'_2=R'_3=CH_3$ and $R=CO_2H$ A suspension of 1.1 g (2.98 mmoles) of 2-methyl 6-(6,7-dimethyl-2-naphthyl) carbonyl naphthalene carboxylate, obtained in Example 2, is stirred for 2 hours in a mixture of 20 cm³ of alcohol and 20 cm³ of 6N aqueous potash heated at reflux. After the addition of 100 cm³ of water, the alcohol is removed by evaporation under a vacuum. The resulting aqueous phase is diluted to 200 cm³, cooled to a temperature between 0 and 5° C. and then acidified with 20 cm³ of 12 N HCl. The resulting precipitate is filtered, washed with water and dried at 80° C. on potash. After recrystallization in isopropanol, 0.67 g of yellow crystals of 6-(6,7-dimethyl-2-naphthyl) carbonyl-2-naphthalene carboxylic acid having a melting point of 275° C. is obtained.

The NMR$^1$H 250 MHz spectrum conforms to the expected structure.

Elemental analysis: $C_{24}H_{18}O_3$

|  | C | H | O |
|---|---|---|---|
| Calculated: | 81.34 | 5.12 | 13.54 |
| Found: | 80.89 | 5.13 | 13.96 |

EXAMPLE 6

Preparation of 6-(6-methoxy-2-naphthyl) carbonyl-2-naphthalene carboxylic acid. Compound of formula III wherein R' and R''=oxo, $R'_1=R'_2=R'_4=H$, $R'_2=R'_3=CH_3$ and $R=CO_2H$ A suspension of 1.5 g (4 mmoles) of 2-methyl 6-(6-methoxy-2-naphthyl) carbonyl naphthalene carboxylate, obtained in Example 1, is stirred for 3 hours in a mixture of 30 cm³ of alcohol and 30 cm³ of 6N aqueous potash heated at reflux. After the addition of 150 cm3 of water, the alcohol is removed by evaporation under a vacuum. The resulting aqueous phase is diluted to 500 cm³, cooled to a temperature between 0 and 5° C. and then acidified by 30 cm³ of 12 N HCl. The resulting precipitate is filtered, washed with water and dried at 80° C. on potash. After recrystallization in an isopropanol/methyl ethyl ketone mixture containing a little acetic acid, 0.75 g of yellow crystals of 6-(6-methoxy-2-naphthyl) carbonyl-2-naphthalene carboxylic acid having a melting point of 174° C. is obtained.

The NMR$^1$H 250 MHz spectrum conforms to the expected structure.

Elemental analysis: $C_{23}H_{16}O_4$

|  | C | H | O |
|---|---|---|---|
| Calculated: | 77.51 | 4.53 | 17.96 |

| | C | H | O |
|---|---|---|---|
| Found: | 77.81 | 4.80 | 17.42 |

EXAMPLE 7

Preparation of N-ethyl 6-(5,8-dimethyl-6-methoxy-2-naphthyl) carbonyl-2-naphthalene carboxamide. Compound of formula III wherein R' and R''=oxo, R'$_1$=R'$_4$=CH$_3$, R'$_2$=H, R'$_3$=OCH$_3$ and R=CONHC$_2$H$_5$ A suspension of 260 mg (0.7 mmole) of 6-(5,8-dimethyl-6-methoxy-2-naphthyl)carbonyl-2-naphthalene carboxylic acid, obtained in Example 4, and 13.5 mg (0.84 mmole) of N,N'- carbonyldiimidazole in 5 cm$^3$ of anhydrous dichloromethane is stirred for 1 hour at ambient temperature. 0.06 cm$^3$ (0.84 mmole) of anhydrous ethylamine is then added to the resulting solution. After stirring for 1 hour, the reaction mixture is diluted to about 130 cm$^3$ to dissolve the amide which has precipitated. The resulting solution is successively washed with 40 cm$^3$ of water, 40 cm$^3$ of 0.5 N HCl and then with 40 cm$^3$ of water. The dichloromethane phase is dried on sodium sulfate and then evaporated to dryness. The crude amide is recrystallized in isopropanol containing a trace of acetic acid. After drying, 260 mg of yellow crystals of N-ethyl 6-(5,8-dimethyl-6-methoxy-2-naphthyl) carbonyl-2-naphthalene carboxamide having a melting point of 236° C. are obtained.

The NMR$^1$H 250 MHz spectrum conforms to the expected structure.

Elemental analysis: C$_{27}$H$_{25}$NO$_3$

| | C | H | N | O |
|---|---|---|---|---|
| Calculated: | 78.81 | 6.12 | 3.40 | 11.67 |
| Found: | 78.71 | 6.16 | 3.30 | 11.93 |

Example 8

Preparation of methyl 4-(5,8-dimethyl-6-methoxy-2-naphthyl) carbonyl benzoate. Compound of formula II wherein n=0, R' and R''=oxo, R'$_1$=R'$_4$=CH$_3$, R'$_2$=H, R'$_3$=OCH$_3$ and R=CO$_2$CH$_3$ (a) 4-methoxycarbonyl benzoic acid To a solution of 20 g of methyl 4-formyl benzoate in 150 cm$^3$ of acetone, there is slowly added a solution containing 30 g of potassium bichromate in 150 cm$^3$ of water and 27 cm$^3$ of concentrated sulfuric acid. Stirring is continued for 2 hours at ambient temperature. After evaporation of the acetone under reduced pressure, the reaction mixture is extracted with ethyl acetate. The organic phase is dried on magnesium sulfate and then concentrated. 11 g of crude 4-methoxy carbonyl benzoic acid are obtained which are then recrystallized in ethyl acetate. The crystals which are filtered and dried have a melting point of 222° C.

The NMR$^1$H spectrum corresponds to the expected structure.

(b) 4-methoxy carbonyl benzoic acid chloride

A suspension of 5 g of the acid, prepared in section (a) above, in 50 cm$^3$ of thionyl chloride is heated for 3 hours at 40° C. At the end of the reaction, the reaction medium is homogenized and the solution is concentrated under reduced pressure. The expected acid chloride crystallizes in the form of pink flakes. The yield is quantitative. This solid is employed directly for the condensation reaction.

(c) To a solution, stirred at a temperature of 5° C., of 5 g (0.0268 mole) of 1,4-dimethyl-2-methoxy naphthalene and 4.85 g (0.0245 mole) of 4-methoxy carbonyl benzoic acid chloride obtained in section (b) above in 200 cm$^3$ of anhydrous 1,2dichloroethane, there are added in small fractions 5.5 g (0.0402 mole) of aluminum chloride. Stirring is continued for ½ hour after the end of the addition. The reaction mixture is left overnight at ambient temperature and then poured over ice. An insoluble precipitate is formed in the two phases which corresponds to 4-methoxy carbonyl benzoic acid. The organic phase is decanted and the aqueous phase extracted with dichloromethane. The organic phases are combined, washed with a solution of sodium bicarbonate and dried on magnesium sulfate.

On concentration of the organic phases under reduced pressure, the expected product crystallizes. On recrystallization in a hexane/toluene mixture 2.1 g of yellow crystals having a melting point of 145° C. are obtained.

EXAMPLE 9

Preparation of 4-(5,8-dimethyl-6-methoxy-2-naphthyl) carbonyl benzoic acid. Compound of formula II wherein n=0, R' and R''=oxo, R'$_1$=R'$_4$=CH$_3$, R'$_2$=H, R'$_3$=OCH$_3$ and R=CO$_2$H A mixture of 1.9 g of the ester obtained in Example 8 and 0.55 g of 85% potash in 50 cm$^3$ of ethanol is heated at reflux for 2 hours. The ethanol is then removed by evaporation under a vacuum. The residue is taken up in 100 cm3 of water and acidified by the addition of concentrated HCl. The expected acid precipitates. It is filtered, dried and then recrystallized in a diisopropyl ether-methyl ethyl ketone mixture. 1.1 g of 4-(5,8-dimethyl- 6-methoxy-2-naphthyl) carbonyl benzoic acid having a melting point of 240° C. are isolated.

The NMR$^1$H 250 MHz spectrum corresponds to the expected structure.

Elemental analysis: C$_{21}$H$_{18}$O$_4$

| | C | H | O |
|---|---|---|---|
| Calculated: | 75.43 | 5.43 | 19.14 |
| Found: | 75.56 | 5.46 | 19.36 |

Example 10

Preparation of N-ethyl 4-(5,8-dimethyl-6-methoxy-2-naphthyl) carbonyl benzamide. Compound of formula II wherein n=0, R' and R''=oxo, R'$_1$=R'$_4$=CH$_3$, R'$_2$=H, R'$_3$=OCH$_3$ and R=CONHC$_2$H$_5$ To a suspension of 500 mg (1.5 moles) of the acid obtained in Example 9 in 50 cm$^3$ of anhydrous dichloromethane, there are added 300 mg (1.8 moles) of carbonyldiimidazole. Stirring is maintained for 3 hours at which point 1 cm$^3$ of anhydrous ethylamine is added. The reaction mixture is left overnight. The dichloromethane is removed by evaporation under a vacuum and the residue is taken up in methyl ethyl ketone. The organic phase is washed with water, dried and concentrated under reduced pressure. The expected product is purified by chromatography on silica gel (eluant: 2-2-1 mixture of toluene-$CH_2Cl_2$-ethyl acetate, respectively). 130 mg of light yellow crystals having a melting point of 210° C. are obtained.

The $NMR^1H$ spectrum corresponds to N-ethyl 4-(5,8-dimethyl-6-methoxy-2-naphthyl) carbonyl benzamide.

EXAMPLE 11

Preparation of 4-(5,8-dimethyl-6-methoxy-2-naphthyl) hydroxymethyl benzoic acid.

Compound of formula II wherein n=0, $R'_1=R'_4=CH_3$, R'=OH, R''=$R'_2$=H, $R'_3=OCH_3$ and R=$CO_2H$ To a solution, stirred at ambient temperature, of 0.5 g of 4-(5,8-dimethyl-6-methoxy-2-naphthyl) carbonyl benzoic acid, obtained in Example 9, in 50 cm³ of methanol there is added, in small portions, 0.25 g of sodium borohydride. Stirring is continued for 1 hour until total disappearance of the initial reactant. The reaction mixture is hydrolyzed with 50 cm³ of water and then acidified with concentrated HCl. After evaporation of the methanol under reduced pressure, the aqueous phase is diluted with 50 cm³ of water and extracted with ethyl acetate. The organic phase is washed with water, dried on magnesium sulfate and concentrated under reduced pressure.

After recrystallization in a hexane-acetone mixture, 250 mg of 4-(5,8-dimethyl-6-methoxy-2-naphthyl) hydroxymethyl benzoic acid having a melting point of 196-197° C. are obtained.

The $NMR^1H$ 80 MHz spectrum conforms to the expected structure.

EXAMPLE 12

Preparation of 4-(5,8-dimethyl-6-methoxy-2-naphthyl) hydroxymethyl phenyl carbinol. Compound of formula II wherein n=0, $R'_1=R'_4=CH_3$, R'=OH, R''=$R'_2$=H, $R'_3=OCH_3$ and R=$CH_2OH$ To a suspension of 3.3 g of lithium aluminum hydride in 200 cm³ of anhydrous tetrahydrofuran maintained at —20° C. there is slowly added a solution of 5.30 g of 4-(5,8-dimethyl-6-methoxy-2-naphthyl) carbonyl benzoic acid, obtained in Example 9, in 150 cm³ of tetrahydrofuran. At the end of the addition stirring of the reaction mixture is continued at ambient temperature until complete disappearance of the starting product and reduction intermediates. After the addition of 50 cm³ of ethyl acetate to eliminate excess hydride, the solution is poured into 200 cm³ of water, acidified and extracted with ethyl acetate. The organic phases are washed, dried on magnesium sulfate and concentrated under reduced pressure. 4 g of 4-(5,8-dimethyl-6-methoxy-2-naphthyl) hydroxymethyl phenyl carbinol are recovered. On recrystallization of a sample in a toluene-hexane mixture, a white powder having a melting point of 140-141° C. is obtained.

The $NMR^1H$ 80 MHz spectrum corresponds to the expected structure.

EXAMPLE 13

Preparation of 4-(5,8-dimethyl-6-methoxy-2-naphthyl) carbonyl benzaldehyde. Compound of formula II wherein n=0, R' and R''=oxo, $R'_1=R'_4=CH_3$, $R'_3=OCH_3$, $R'_2$=H and R=CH=O To a supension of 3.5 g of 4-(5,8-dimethyl-6-methoxy-2-naphthyl) hydroxymethyl phenylcarbinol, obtained in Example 12, in 200 cm³ of anhydrous dichloromethane, there are added 8.5 g of pyridinium chlorochromate.

Stirring is maintained for about 4 hours until complete disappearance of the starting product. After addition of about 20 grams of silica and 300 cm³ of dichloromethane, the solution is filtered, washed with a solution of ammonium chloride and water, then dried on magnesium sulfate and concentrated under reduced pressure. An oil which crystallizes in diisopropyl oxide is recovered.

There is thus obtained a yellow powder having a melting point of 139-140° C. whose $NMR^1H$ 80 MHz spectrum corresponds to the expected structure of 4-(5,8-dimethyl-6-methoxy-2-naphthyl) carbonyl benzaldehyde.

EXAMPLE 14

Preparation of trans ethyl 4-(5,8-dimethyl-6-methoxy-2-naphthyl) carbonyl α-methyl cinnamate. Compound of formula II wherein n=1, R' and R''=oxo, $R'_1=R'_4=R'_7=CH_3$, $R'_3=OCH_3$, $R'_2$=H and R=$CO_2C_2H_5$ To a solution of 1.5 cm³ of 2-triethyl phosphonopropionate in 100 cm³ of anhydrous tetrahydrofuran, there is added in small portions 0.4 g of sodium hydride. A gaseous emission is observed. Stirring is maintained for about 1 hour, and then in the absence of light there are added a few drops of ring ether and a solution of 1.4 g of 4-(5,8-dimethyl-6-methoxy-2-naphthyl) carbonyl benzaldehyde, obtained in Example 13, in solution in 50 cm³ of anhydrous tetrahydrofuran. At the end of the addition, stirring is maintained for 2 hours and the reaction mixture is poured into a saturated solution of ammonium chloride and extracted with ethylacetate. The organic phases are washed, dried and concentrated under reduced pressure.

The expected product crystallizes in a hexane-diisopropyl oxide mixture and has a melting point of 112-114° C.

The $NMR^1H$ 80 MHz spectrum corresponds to the structure of trans ethyl 4-(5,8-dimethyl-6-methoxy-2-naphthyl) carbonyl α-methyl cinnamate.

EXAMPLE 15

Preparation of trans 4-(5,8-dimethyl-6-methoxy-2-naphthyl) carbonyl α-methyl cinnamic acid. Compound of formula II wherein n=1, R' and R''=oxo, $R'_1=R'_4=R'_7=CH_3$, $R'_3=OCH_3$, $R'_2$=H and R=$CO_2H$ A suspension of 1.1 g of trans ethyl 4-(5,8-dimethyl-6-methoxy-2-naphthyl) carbonyl α-methyl cinnamate, obtained in Example 14, is stirred for 2 hours in a mixture of 100 cm³ of ethanol and 25 cm³ of 6N aqueous potash at a temperature between 40 and 50° C. After evaporation of the ethanol under reduced pressure, the residue is taken up in 500 cm³ of water and acidified with 3N HCl. The resulting precipitate is filtered, thoroughly washed with water and dried.

There is recovered 1 g of acid which, after recrystallization in toluene, has a melting point of 190-191° C.

Elemental analysis: $C_{24}H_{22}O_4$

| | C | H | O |
| --- | --- | --- | --- |
| Calculated: | 76.98 | 5.92 | 17.09 |
| Found: | 77.07 | 5.98 | 17.09 |

Example 16

Preparation of N-ethyl 6-(5,8-dimethyl-6-methoxy-2-naphthyl) hydroxymethyl-2-naphthalene carboxamide. Compound of formula III wherein R'=OH, R''=H, $R'_1=R'_4=CH_3$, $R'_2=H$, $R'_3=OCH_3$ and $R=CONHC_2H_5$ To a solution of 0.74 g (1.8 mmoles) of N-ethyl 6-(5,8-dimethyl-6-methoxy-2-naphthyl) carbonyl-2-naphthalene carboxamide, obtained in Example 7, in 25 cm³ of anhydrous tetrahydrofuran, stirred at ambient temperature, there is added 0.3 g (8 mmoles) of sodium borohydride. After stirring overnight at ambient temperature the reaction mixture is heated for 3 hours at reflux. The reduction is then complete and the reaction mixture is cooled to a temperature between 0 and 5° C., acidified by the slow addition of 0.1N HCl and extracted with ethyl ether. The organic phase is washed with water, dried on sodium sulfate and evaporated to dryness. The resulting solid is recrystallized in isopropyl alcohol. After drying, 0.55 g of white crystals of N-ethyl 6-(5,8-dimethyl-6-methoxy-2-naphthyl) hydroxymethyl-2-naphthalene carboxamide having a melting point of 198° C. is obtained.

The NMR¹H 250 MHz spectrum conforms to the expected structure.

Elemental analysis: $C_{27}H_{27}NO_3$

|  | C | H | N | O |
| --- | --- | --- | --- | --- |
| Calculated: | 78.42 | 6.58 | 3.39 | 11.61 |
| Found: | 78.26 | 6.62 | 3.32 | 11.48 |

EXAMPLE 17

Preparation of 6-(5,8-dimethyl-6-methoxy-2-naphthyl) hydroxymethyl-2-naphthalene carboxylic acid. Compound of formula III wherein R'=OH, R''=H, $R'_1=R'_4=CH_3$, $R'_2=H$, $R'_3=OCH_3$ and $R=CO_2H$ To a solution of 0.77 g (2 mmoles) of 6-(5,8-dimethyl-6-methoxy-2-naphthyl) carbonyl-2-naphthalene carboxylic acid, obtained in Example 4, in 25 cm³ of anhydrous tetrahydrofuran, stirred at ambient temperature, there is added 0.3 g (8 mmoles) of sodium borohydride. After stirring for 30 hours the reaction mixture is cooled to a temperature between 0 and 5° C., acidified by the slow addition of 0.2N HCl and extracted with ethyl ether. The organic phase is washed with water, dried on magnesium sulfate and evaporated to dryness. The resulting crude solid is recrystallized in isopropyl alcohol containing a little methyl ethyl ketone. After drying, 0.58 g of white crystals of 6-(5,8- dimethyl-6-methoxy-2-naphthyl) hydroxymethyl-2-naphthalene carboxylic acid having a melting point of 223-225° C. is obtained.

The NMR¹H 250 MHz spectrum conforms the expected structure.

Elemental analysis: $C_{25}H_{22}O_4$

|  | C | H | O |
| --- | --- | --- | --- |
| Calculated: | 77.70 | 5.74 | 16.56 |
| Found: | 77.31 | 5.85 | 16.22 |

EXAMPLE 18

Preparation of 6-(5,8-dimethyl-6-methoxy-2-naphthyl) hydroxymethyl-2-naphthalene carbinol. Compound of formula III wherein R'=OH, R''=H, $R'_1=R'_4=CH_3$, $R'_2=H$, $R'_3=OCH_3$ and $R=CH_2OH$ To a suspension of 230 mg (6 mmoles) of lithium aluminum hydride in 25 cm³ of anhydrous tetrahydrofuran, cooled to −5° C., there is added 0.65 g(1.7 mmoles) of 6-(5,8-dimethyl-6-methoxy-2-naphthyl) carbonyl-2-naphthalene carboxylic acid obtained in Example 4. After stirring for 6 hours and letting the reaction mixture return to ambient temperature, the reaction mixture is cooled to 0° C., acidified by the slow addition of 0.1N HCl and extracted with ethyl ether. The organic phase is washed with water, dried on sodium sulfate and evaporated to dryness. The resulting crude solid is purified by chromatography on silica gel 60 using the following eluant mixture: 2:8:90, acetic acid/dioxan/toluene, respectively, followed by a recrystallization in a hexane-/acetone mixture. After drying, 0.45 g of white crystals of 6-(5,8-dimethyl-6-methoxy-2- naphthyl)hydroxymethyl-2-naphthalene carbinol having a melting point of 164-165° C. is obtained.

The IR and NMR¹H spectra conform to the expected structure.

EXAMPLE 19

Preparation of 1-(5,8-dimethyl-6-methoxy-2-naphthyl)-1-(6-carboxy-2-naphthyl) methane. Compound of formula III wherein $R'=R''=R'_2=H$, $R'_1=R'_4=CH_3$, $R'_3=OCH_3$ and $R=CO_2H$ To a suspension of 2.5 g (37.5 mmoles) of powdered zinc in 25 cm³ of glacial acetic acid there is added 0.96 g (2.5 mmoles) of 6-(5,8-dimethyl-6-methoxy-2-naphthyl) carbonyl-2-naphthalene carboxylic acid obtained in Example 4. The reaction mixture is heated for 1 hour at reflux. There are then slowly added 2.5 cm³ of 12N HCl and reflux is maintained for 1 hour. After cooling to ambient temperature and adding 50 cm³ of 6N HCl, the reaction mixture is extracted with dichloromethane (2×100 cm³). The organic phase is washed with water, dried on sodium sulfate and concentrated under reduced pressure. The isolated yellow solid is purified by chromatography on silica gel 60 with an elution using an 80/20 mixture of dichloromethane/ethylacetate followed by a recrystallization in isopropyl alcohol. After drying, 0.62 g of white crystals of 1-(5,8-dimethyl-6-methoxy-2-naphthyl)-1-(6-carboxy-2-naphthyl) methane having a melting point of 179° C. is obtained.

The NMR¹H 250 MHz spectrum conforms to the expected structure.

EXAMPLE 20

Preparation of 1-(5,8-dimethyl-6-methoxy-2-naphthyl)-1-(6-N-ethylcarboxamide-2-naphthyl) methane. Compound, of formula III wherein $R'=R''=R'_2=H$, $R'_1=R'_4=CH_3$, $R'_3=OCH_3$ and $R=CONHC_2H_5$ To a suspension of 2.5 g (37.5 mmoles) of powdered zinc in 25 cm³ of glacial acetic acid, there is added 1 g (2.43 mmoles) of N-ethyl 6-(5,8-dimethyl-6-methoxy-2-naphthyl) carbonyl-2naphthalene carboxamide obtained in Example 7. The reaction mixture is heated for 1 hour at reflux. There are then slowly added 2.5 cm³ of 12 N HCl and reflux is maintained for 20 minutes. After cooling to ambient temperature and adding 80 cm³ of 6N HCl, the reaction mixture is extracted with dichloromethane. The organic phase is washed with water, dried on sodium sulfate and concentrated under reduced pressure. The recovered yellow solid is rapidly purified by chromatography on silica gel 60 using initially as the eluant dichloromethane and then a 95/5 mixture of dichloromethane/ethylacetate. After evaporation, the isolated white solid is recrystallized in a hexane/acetone mixture. After drying, 0.64 g of white crystals of 1-(5,8-dimethyl-6-methoxy-2-naphthyl)-1-(6-N-ethylcarboxamide-2-naphthyl) methane having a melting point of 166° C. is obtained.

The NMR$^1$H 250 MHz spectrum conforms to the expected structure.

Examples of Compositions

| A. Oral compositions | |
|---|---|
| Example I - 0.2 g tablet | |
| 6-(5,8-dimethyl-6-methoxy-2-naphthyl) carbonyl-2-naphthalene carboxylic acid | 0.005 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| Example II - Drinkable suspension in 5 ml ampoules | |
| Trans 4-(5,8-dimethyl-6-methoxy-2-naphthyl) carbonyl α-methyl cinnamic acid | 0.005 g |
| Glycerine | 0.500 g |
| Sorbitol, 70% | 0.500 g |
| Sodium saccharinate | 0.010 g |
| Methyl parahydroxybenzoate | 0.040 g |
| Flavoring agent, sufficient amount | |
| Purified water, sufficient amount for | 5.000 ml |
| B. Topical Compositions | |
| Example III - Ointment | |
| Methyl 6-(5,8-dimethyl-6-methoxy-2-naphthyl) carbonyl-2-naphthalene carboxylate | 0.020 g |
| Isopropyl myristate | 81.700 g |
| Fluid petrolatum oil | 9.100 g |
| Silica, sold under the trade name "Aerosil 200" by Degussa | 9.180 g |
| Example IV - Anionic oil-in-water cream | |
| N—ethyl trans 4-(5,8-dimethyl-6-methoxy-2-naphthyl) carbonyl α-methyl cinnamide | 0.100 g |
| Sodium dodecyl sulfate | 0.800 g |
| Glycerol | 2.000 g |
| Stearylic acid | 20.000 g |
| Triglycerides of capric/caprylic acids sold under the trade name "Myglyol 812" by Dynamit Nobel | 20.000 g |
| Preservative, sufficient amount | |
| Demineralized water, sufficient amount for | 100.000 g |

In this example the active compound can be replaced by the same amount of 4-(5,8-dimethyl-6-methoxy-2-naphthyl) carbonyl benzoic acid.

| Example V - Gel | |
|---|---|
| N—ethyl 6-(5,8-dimethyl-6-methoxy-2-naphthyl)-2-naphthalene carboxamide | 0.05 g |
| Hydroxypropyl cellulose, sold under the trade name "Klucel HF" by Hercules | 2.000 g |
| Water/ethanol, 50/50, sufficient amount for | 100.000 g |

In this example the active compound can be replaced by 0.2 g of N—ethyl 4-(5,8-dimethyl-6-methoxy-2-naphthyl) carbonyl benzamide.

| Example VI - Anti-seborrhea cream | |
|---|---|
| Polyoxyethylenated stearate (40 moles of of ethylene oxide), sold under the trade name "Myrj 52" by Atlas | 4.000 g |
| Mixture of lauryl esters of sorbitol and sorbitan, polyoxyethylenated with 20 moles of ethylene oxide, sold under the trade name "Tween 20" by Atlas | 1.800 g |
| Mixture of mono- and distearate of glycerol, sold under the trade name "GELEOL" by Gattefosse | 4.200 g |
| Propylene glycol | 10.000 g |
| Butylhydroxy anisole | 0.010 g |
| Butylhydroxy toluene | 0.020 g |
| Cetyl stearyl alcohol | 6.200 g |
| Preservatives, sufficient amount | |
| Perhydrosqualene | 18.000 g |
| Mixture of caprylic/capric triglycerides, sold under the trade name "Miglyol 812" by Dynamit Nobel | 4.000 g |
| S—carboxymethyl cysteine | 3.000 g |
| Triethanolamine, 99% | 2.500 g |
| 6-(5,8-dimethyl-6-methoxy-2-naphthyl) hydroxymethyl-2-naphthalene carboxylic acid | 0.200 g |
| Water, sufficient amount for | 100.000 g |
| Example VII - Anti-seborrhea cream | |
| Polyoxyethylenated stearate (40 moles of ethylene oxide), sold under the trade name "Myrj 52" by Atlas | 4.000 g |
| Mixture of lauryl esters of sorbitol and sorbitan, polyoxyethylenated with 20 moles of ethylene oxide, sold under the trade name "Tween 20" by Atlas | 1.800 g |
| Mixture of mono- and distearate of glycerol, sold under the trade name "GELEOL" by Gattefosse | 4.200 g |
| Propylene glycol | 10.000 g |
| Butylhydroxy anisole | 0.010 g |
| Butylhydroxy toluene | 0.020 g |
| Cetyl-stearyl alcohol | 6.200 g |
| Preservatives, sufficient amount | |
| Perhydrosqualene | 18.000 g |
| Mixture of caprylic/capric triglycerides, sold under the trade name "Miglyol 812" by Dynamit Nobel | 4.000 g |
| 5-amino-5-carboxy-3-thia pentanoate of 2-benzylthio ethylammonium | 3.000 g |
| N—ethyl 4-(5,8-dimethyl-6-methoxy-2-naphthyl) carbonyl α-methyl cinnamide | 0.500 g |
| Water, sufficient amount for | 100.000 g |
| Example VIII - Hair lotion | |
| Propylene glycol | 20.000 g |
| Ethanol | 34.87 g |
| Polyethylene glycol, molecular mass 400 | 40.000 g |
| Water | 4.000 g |
| Buthylhydroxy anisole | 0.010 g |
| Butylhydroxy toluene | 0.020 g |
| 4-(5,8-dimethyl-6-methoxy-2-naphthyl) carbonyl α-methyl cinnamic acid | 0.100 g |
| Minoxidil | 1.000 g |
| Example IX - Anti-acne gel | |
| 4-(5,8-dimethyl-6-methoxy-2-naphthyl) carbonyl α-methyl cinnamic acid | 0.100 g |
| Isopropyl alcohol | 40.000 g |
| Acrylic acid polymer, sold under the trade name "Carbopol 940" by Goodrich Chemical Co. | 1.000 g |
| Triethanolamine, 99% | 0.600 g |
| Butylhydroxy anisole | 0.010 g |
| Butylhydroxy toluene | 0.020 g |
| Tioxolone | 0.500 g |
| Propylene glycol | 8.000 g |
| Purified water, sufficient amount for | 100.000 g |

What is claimed is:

1. An aromatic naphthyl compound having the formula

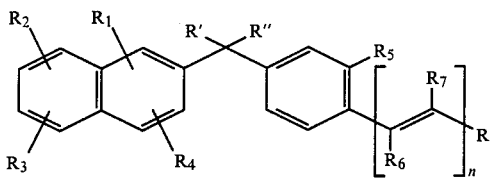 (I)

wherein
n is 0 or 1,
R' represents hydrogen, OH, acyloxy, lower alkoxy or $NH_2$,
R" represents hydrogen or lower alkoxy or R' and R" taken together from an oxo radical, a methano radical or a hydroxyimino radical,
R represents —$CH_2OH$ or —$COR_8$,
$R_8$ represents hydrogen, —$OR_9$ or

$R_9$ represents hydrogen, linear or branched alkyl having 1-20 carbon atoms, mono or polyhydroxy alkyl, aryl, aryl substituted by halogen, hydroxy or nitro, aralkyl, the residue of a sugar or a radical having the formula

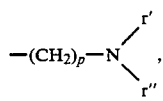

p is 1,2 or 3,
r' and r" each independently represent hydrogen, lower alkyl, monohydroxyalkyl, monohydroxyalkyl interrupted by a heteroatom, polyhydroxyalkyl, aryl, aryl substituted by halogen, hydroxy or nitro, benzyl, the residue of an amino acid or the residue of an aminated sugar, or r' and r" taken together form a heterocycle,
$R_1$, $R_2$, $R_3$ and $R_4$ each independently represent hydrogen, lower alkyl, alkoxy having 1-4 carbon atoms, lower fluoroalkoxy, $CF_3$, cycloalkyl. lower acyl, halogen, OH, amino, lower acylamino or lower alkoxy carbonyl,
the substituents $R_1$ to $R_4$ being able to be distributed on one of the two rings or on both at the same time,
$R_5$, $R_6$ and $R_7$ represent hydrogen or methyl or when n=1, $R_5$ and $R_7$ taken together can form with the benzene ring a naphthalene ring, and
the salts of said compound of formula I or its geometric or optical isomers.

2. The compound of claim 1 in the form of an alkali metal salt, an alkaline earth metal salt, a zinc salt, an organic amine salt, a mineral acid salt or an organic acid salt.

3. The compound of claim 1 wherein said lower alkyl has 1-6 carbon atoms.

4. The compound of claim 3 wherein said lower alkyl is methyl, ethyl, isopropyl, butyl or tert.butyl.

5. The compound of claim 1 whrein said monohydroxy alkyl has 2-6 carbon atoms.

6. The compound of claim 5 wherein said monohydroxy alkyl is 2-hydroxyethyl, 2-hydroxy propel or 2-hydroxy ethoxy ethyl.

7. The compound of claim 1 wherein said polyhydroxy alkyl has 3-6 carbon atoms.

8. The compound of claim 7 wherein said polyhydroxy alkyl is 2,3-dihydroxy propyl, 1,3-dihydroxy propyl or the residue of pentaerythritol.

9. The compound of claim 1 wherein said cylcoalkyl has 5-12 carbon atoms.

10. The compound of claim 9 wherein said cycloalkyl is cyclopentyl, cyclohexyl or adamantyl.

11. The compound of claim 1 wherein r' and r" taken together form a heterocycle selected from the group consisting of piperidino, piperazino, morpholino, pyrrolidino and 4-(2-hydroxy ethyl) piperazino.

12. The compound of claim 1 having the formula

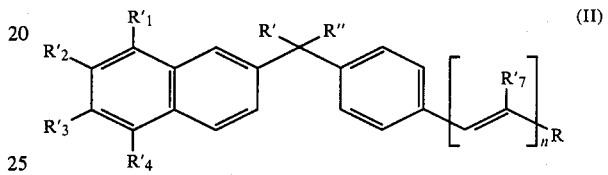 (II)

wherein n is 0 or 1,
$R'_1$, $R'_2$ and $R'_4$ represent hydrogen or lower alkyl,
$R'_3$ represents lower alkyl or lower alkoxy,
R' represents hydrogen or OH and R" represents hydrogen or R' and R" together form an oxo radical and R represents —$CH_2OH$ or $COR'_8$,
$R'_8$ represents -$OR'_9$ or

$R'_9$ represents hydrogen or lower alkyl,
r' represents hydrogen and
r" represents lower alkyl.

13. The compound of claim 1 having the formula

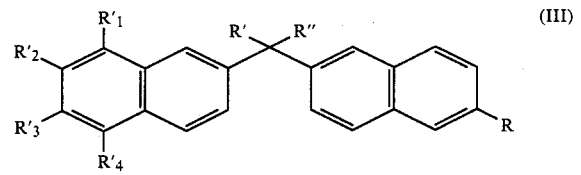 (III)

wherein
$R'_1$, $R'_2$ and $R'_4$ represent hydrogen or lower alkyl, $R'_3$ represents lower alkyl or lower alkoxy, R' represents hydrogen or OH and R" represents hydrogen or R' and R" together form an oxo radical and R represents —$CH_2OH$ or —$COR'_8$, $R'_8$ represents —$OR'_9$ or

$R'_9$ represents hydrogen or lower alkyl,
r' represents hydrogen and
r" represents lower alkyl.

14. The compound of claim 1 selected form the group consisting of
(1) 2-methyl 6-(6,7-dimethyl-2-naphthyl) carbonyl naphthalene carboxylate,
(2) 6-(6,7-dimethyl-2-naphthyl) carbonyl-2-naphthalene carboxylic acid,
(3) 2-nethyl 6-(5,8-dimethyl-6-methoxy-2-napgthyl) carbonyl naphthalene carboxylate,
(4) 6-(5,8-dimethyl-6-methoxy-2-naphthyl) carbonyl-2-naphthalene carboxylic acid,
(5) N-ethyl-6-(5,8-dimethyl-6-methoxy-2-naphthyl) carbonyl-2-naphthalene carboxamide,
(6) 6-(6-methoxy-2-naphthyl) carbonyl-2-methyl naphthalene carboxylate,
(7) 6-(6-methoxy-2-naphthyl) carbonyl-2-naphthalene carboxylic acid,
(8) 6-(5,8-dimethyl-6-methoxy-2-naphthyl) hydroxymethyl-2-naphthalene carboxylic acid,
(9) N-ethyl-6-(5,8-dimethyl-6-methoxy-2-naphthyl) hydroxymethyl-2-naphthalene carboxamide,
(10) 6-(5,8-dimethyl-6-methoxy-2-naphthyl) hydroxy methyl-2-naphthalene carbinol,
(11) trans ethyl-4-(5,8-dimethyl-6-methoxy-2-naphthyl) carbonyl-α-methyl cinnamate,
(12) trans-4-(5,8-dimethyl-6-methoxy-2-naphthyl) carbonyl-α-methylcinnamic acid,
(13) N-ethyl trans 4-(5,8-dimethyl-6-methoxy-2-naphthyl) carbonyl-α-methyl cinnamide,
(14) trans 4-(5,8-dimethyl-6-methoxy-2-naphthyl) hydroxy methyl-α-methyl cinnamic acid,
(15) methyl 4-(5,8-dimethyl-6-methoxy-2-naphthyl) carbonyl benzoate,
(16) 4-(5,8-dimethyl-6-methoxy-2-naphthyl) carbonyl benzoic acid,
(17) 4-(5,8-dimethyl-6-methoxy-2-naphthyl) hydroxymethyl benzoic acid,
(18) 4-(5,8-dimethyl-6-methoxy-2-naphthyl) hydroxymethyl phenyl carbinol,
(19) 4-(5,8-dimethyl-6-methoxy-2-naphthyl) carbonyl benzaldehyde,
(20) N-ethyl-4-(5,8-dimethyl-6-methoxy-2-naphthyl) carbonyl benzamide,
(21) 1-(5,8-dimethyl-6-methoxy-2-naphthyl)-1-(6-carboxy-2-naphthyl) methane and
(22) 1-(5,8-dimethyl-6-methoxy-2-naphthyl)-1-(6-N-ethyl carboxamide-2-naphthyl) methane.

15. A process for preparing the compound of claim 1 comprising reacting in an organic solvent a halide having one of the following two formulas:

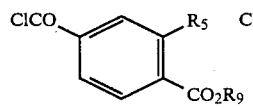 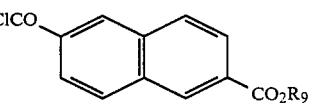

wherein
R5 has the meaning given in claim 1 and R9 is alkyl having 1–20 carbon atoms with a naphthalene derivative having one of the following two formulas:

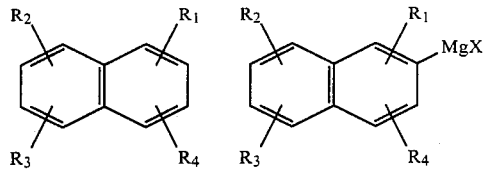

wherein
R1 to R4 have the same meanings given in claim 1 and X is Br or Cl,
saponifying, if necessary, the resulting keto-ester into the corresponding keto-acid and
subsequently transforming said keto-acid into the corresponding amide by reaction with an amine of the formula

wherein r' and r" have the meanings given in claim 1 or subsequently transforming said keto-acid into a hydroxy acid or diol and
if necessary oxidizing said diol into the corresponding keto-aldehyde.

16. The process of claim 15 wherein the condensation reaction is carried out under Friedel-Crafts reaction conditions in the presence of anhydrous aluminum chloride in 1,2-dichloroethane at a temperature ranging between 0 and 25° C. with stirring.

17. The process of claim 15 wherein the condensation of the acid chloride with the organo magnesium compound is carried out in THF at a temperature of about 0° C.

18. The process of claim 15 wherein the preparation of the amide is carried out in the presence of N,N'-carbonyl diimidazole.

19. The process of claim 15 wherein the reduction of the keto-acid to the corresponding hydroxy acid is carried out in the presence of sodium borohydride in THF.

20. The process of claim 15 wherein the keto-aldehyde is obtained by oxidation of said diol using pyridinium chlorochromate, the corresponding diol resulting from the reduction reaction of the keto-acid in the presence of lithium aluminum hydride.

21. A process for the preparation of a compound of the formula:

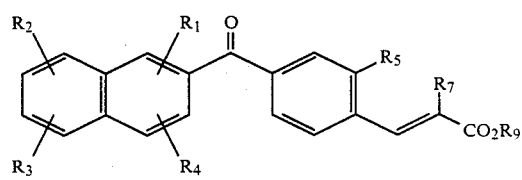

comprising reacting a keto-aldehyde having the formula

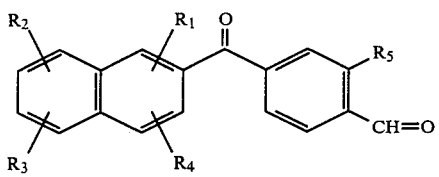

wherein $R_1$-$R_5$ have the meanings given in claim 1, with an alkyl phosphono acetate of the formula

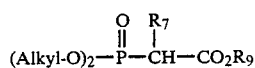

wherein $R_7$ and $R_9$ have the meanings given in claim 1, in the presence of sodium hydride in THF and submitting the resulting unsaturated keto-ester to suitable reactions to produce the compound of claim 1.

22. A medicine comprising the compound of claim 1 and a medicinally acceptable vehicle.

23. A medicine in daily dosage form of about 2 μg/kg to 2 mg/kg of body weight comprising the compound of claim 1 and medicinally acceptable vehicle.

24. A pharmeceutical composition comprising in a pharmaceutically acceptable vehicle suitable for enteral, parenteral, topical or ocular administration an effective amount of the compound of claim 1.

25. The composition of claim 24 wherein said vehicle is suitable for topical or ocular administration and said compound is present in an amount ranging from 0.005 to about 5 percent by weight based on the total weight of said composition.

26. A cosmetic composition for body and hair hygiene comprising in a cosmetically acceptable vehicle an effective amount of the compound of claim 1.

27. The cosmetic composition of claim 26 wherein said compound is present in an amount ranging from 0.0005 to 2 percent by weight based on the total weight of said composition.

28. A process for the treatment of dermatologic, respiratory or opthalmologic disorders comprising administering to a person suffering from said disorders an effective amount of the compound of claim 1.

* * * * *